US008518696B2

(12) United States Patent
Lau et al.

(10) Patent No.: US 8,518,696 B2
(45) Date of Patent: Aug. 27, 2013

(54) PRODUCTION OF HOMOGENEOUS CELL LINE HIGHLY PERMISSIVE TO PORCINE CIRCOVIRUS TYPE 2 (PCV2) INFECTION

(75) Inventors: Adeline Hui Ling Lau, Singapore (SG); Jennifer Siew Kee Lau, Singapore (SG); Hwei-Sing Kwang, Singapore (SG)

(73) Assignee: Temasek Life Sciences Laboratory Limited, Singapore (SG)

( * ) Notice: Subject to any disclaimer, the term of this patent is extended or adjusted under 35 U.S.C. 154(b) by 603 days.

(21) Appl. No.: 12/599,555

(22) PCT Filed: May 11, 2007

(86) PCT No.: PCT/SG2007/000133
§ 371 (c)(1),
(2), (4) Date: Sep. 16, 2010

(87) PCT Pub. No.: WO2008/140414
PCT Pub. Date: Nov. 20, 2008

(65) Prior Publication Data
US 2011/0008871 A1    Jan. 13, 2011

(51) Int. Cl.
*C12N 5/12*      (2006.01)
*C12Q 1/68*      (2006.01)
(52) U.S. Cl.
USPC .......... 435/325; 435/235.1; 435/5; 424/130.1
(58) Field of Classification Search
None
See application file for complete search history.

(56) References Cited

U.S. PATENT DOCUMENTS

| | | | | |
|---|---|---|---|---|
| 6,573,081 | B2 * | 6/2003 | Bernhardt et al. | 435/235.1 |
| 6,794,163 | B2 * | 9/2004 | Liu et al. | 435/70.1 |
| 7,172,899 | B2 * | 2/2007 | Liu et al. | 435/325 |
| 7,300,785 | B2 * | 11/2007 | Meerts et al. | 435/239 |
| 7,566,562 | B2 * | 7/2009 | Nauwynck et al. | 435/235.1 |
| 2002/0055189 | A1 * | 5/2002 | Bernhardt et al. | 436/548 |
| 2003/0186307 | A1 * | 10/2003 | Bernhardt et al. | 435/6 |
| 2007/0161005 | A1 * | 7/2007 | Meerts et al. | 435/6 |
| 2007/0184544 | A1 * | 8/2007 | Nauwynck et al. | 435/235.1 |
| 2008/0226594 | A1 * | 9/2008 | Nauwynck et al. | 424/85.4 |
| 2008/0241821 | A1 * | 10/2008 | Allibert et al. | 435/5 |
| 2010/0172924 | A1 * | 7/2010 | Jestin et al. | 424/186.1 |

FOREIGN PATENT DOCUMENTS

| | | |
|---|---|---|
| AU | 756554 | 4/1999 |
| RU | 2201960 C2 | 4/2003 |
| WO | 2006113435 A2 | 10/2006 |
| WO | 2006132605 A2 | 12/2006 |

OTHER PUBLICATIONS

Grummer B, Fischer S, Depner K, Riebe R, Blome S, Greiser-Wilke I. Replication of classical swine fever virus strains and isolates in different porcine cell lines. Dtsch Tierarztl Wochenschr. Apr. 2006;113(4):138-42.*
Tischer I, Peters D, Rasch R, Pociuli S. Replication of porcine circovirus: induction by glucosamine and cell cycle dependence. Arch Virol. 1987;96(1-2):39-57.*
Kim HS, Kwang J, Yoon IJ, Joo HS, Frey ML. Enhanced replication of porcine reproductive and respiratory syndrome (PRRS) virus in a homogeneous subpopulation of MA-104 cell line. Arch Virol. 1993;133(3-4):477-83.*
Cheung, A.K., et al., "Kinetics of porcine circovirus type 2 replication," Archives of Virology, 147(1): 43-58 (2002).
Meehan, Brian M., et al., "Characterization of novel circovirus DNAs associated with wasting syndromes in pigs," Journal of General Virology, 79 (Pt. 9):2171-2179 (Sep. 1998).
Cheung, Andrew K., Transcriptional Analysis of Porcine Circovirus Type 2, Virology, 305(1): 168-180 (2003).
Mateusen, B., et al., "Susceptibility of pig embryos to porcine circovirus type 2 infection," Theriogenology, 61(1): 91-101 (Jan. 2004).
Hirai, Takuya, et al., "Infectivity of Porcine Circovirus 1 and Circovirus 2 in Primary Porcine Hepatocyte and Kidney Cell Cultures," The Journal of Veterinary Medical Science, 68(2): 179-182 (Feb. 2006).
ATCC Technical Bulletin 7, "Passage Number Effects in Cell lines," (2007) Retrieved from Internet: URL:http://www.genengnews.com/transfection/ATCC_TechBulletin_7_Final_06_07.pdf.
Dezengrini, Renata, et al., "Selection and characterization of canine, swine and rabbit cell lines resistant to bovine viral diarrhea virus," Journal of Virological Methods, 137: 51-57 (2006).
Tischer, Ilse, et al., "Replication of porcine circovirus: induction by glucosamine and cell cycle dependence," Archives of Virology, 96: 39-57 (1987).
European Patent Office Official Action for European Application No. 07748678.5-2405 dated Feb. 28, 2011.
Zhu, Yu, "Enhanced replication of porcine circovirus type 2 (PCV2) in a homogeneous subpopulation of PK15 cell line," Virology, 369(2): 423-430 (2007).
Kim, H.S., et al., "Enhanced replication of porcine reproductive and respiratory syndrome (PRRS) virus in a Homogeneous subpopulation of MA-104 cell line," Archives of Virology, 133: 477-483 (Jan. 1, 1993).
Supplementary European Search Report for EP 07748678, dated Jun. 11, 2010.

* cited by examiner

*Primary Examiner* — Benjamin P Blumel
*Assistant Examiner* — Rachel Gill
(74) *Attorney, Agent, or Firm* — Rothwell, Figg, Ernst & Manbeck, P.C.

(57) ABSTRACT

Continuous cell lines that are highly permissive to infection by porcine circovirus type 2 ("PCV2") are described. PCV2 is the causal agent of post-weaning multi-systemic wasting syndrome ("PMWS") in pigs. PMWS has emerged as a major disease that poses a significant threat to the economics of global swine industry. The highly permissive cell lines of this invention provide efficient and reliable sources of PCV2 for use in development of vaccines, therapies and diagnostic agents for PMWS.

3 Claims, 3 Drawing Sheets

PRODUCTION OF HOMOGENEOUS CELL LINE HIGHLY PERMISSIVE TO PORCINE CIRCOVIRUS TYPE 2 (PCV2) INFECTION

This application is a filing under 35 USC §371 of PCT/SG2007/000133, filed May 11, 2007. This application is incorporated herein by reference.

BACKGROUND OF THE INVENTION

The present invention relates to the production of porcine circovirus type 2 (PCV2). More particularly, the invention relates to continuous cell lines that are highly susceptible to infection with PCV2 and to methods for the production of PCV2 using the cell lines.

Porcine circovirus (PCV) is a small, non-enveloped, circular, single-stranded DNA virus classified in the Circoviridae family. Murphy, F A., Fauquet, C M., Bishop, D H L., Ghabrial, S A., Jarvis, A W., Martelli, G P.; Mayo, M A., Summers, M D. *Virus taxonomy. Sixth report of the International Committee on Taxonomy of Viruses*. New York, N.Y: Springer-Verlag; 1995. pp. 166-168. It was originally identified and described as a contaminant of a porcine kidney cell line. Tischer, I., Gelderblom, H., Vettermann, W., Koch, M. A. *A very small porcine virus with circular single-stranded DNA. Nature.* 1982:295:64-66. Recently, PCV has been associated with a disease of pigs, the post-weaning multi-systemic wasting syndrome (PMWS), first observed in Western Canada. Ellis, J., Hassard, L., Clark, E., Harding, J., Allan, G., Willson, P., Strokappe, J., Martin, K., McNeilly, F., Meehan, F., Todd, D., Haines, D. *Isolation of circovirus from lesions of pigs with postweaning multisystemic wasting syndrome. Can. Vet. J.,* 1998; 39:44-51; Harding, J. C. S., Clark, E. G. *Recognizing and diagnosing postweaning multisystemic wasting syndrome (PMWS). Swine Health Prod.* 1997; 5:201-203; Jue Liu, Isabelle Chen, and Jimmy Kwang, *J. Virol.* 2005: 79(13); 8262-74. PWMS has emerged as a major disease that poses a significant threat to the economics of the global swine industry. After its first appearance in Canada, PMWS has now spread to the United States, Europe and Asia. The syndrome mainly affects pigs between 6 and 14 weeks of age. It tends to be slow and progressive with a high fatality rate in affected pigs. See http:www dot aphis dot usda dot gov/vs/ceah backslash dei/taf backslash emergingdiseasenotice_files/pmws_0301.htm.

The clinical signs of PMWS are quite variable. Affected pigs may show signs of chronic wasting, respiratory distress, diarrhea, incoordination, paralysis, pale skin color and blue ears. Pigs usually demonstrate a decrease in growth rate and, occasionally, jaundice.

The diagnosis of PMWS is based on the age of affected pigs, typical wasting appearance and necropsy lesions. Microscopic and immunohistochemical examination of tissues reveals unique lung and lymphoid tissue lesions with the presence of PCV2. Id.

Antibacterial medication is usually ineffective in treating PWMS and currently no vaccines are available. Prevention of the syndrome is based on biosecurity precautions and good husbandry practices.

PCV2 has also been found in association with other diseases including porcine dermatitis and nephropathy syndrome ("PDNS"), congenital tremors (CT-All) reproductive disorders, prenatal myocarditis and proliferative and necrotizing pneumonia.

Vaccines employing PCV2 antigens have shown some initial success in preventing the PMWS. Fenaux, M., et al., *A chimeric porcine circovirus (PCV) with the immunogenic capsid gene of the pathogenic PCV type 2 (PCV2) cloned into the genomic backbone of the nonpathogenic PCV1 induces protective immunity against PCV2 infection in pigs. J. Virol.,* 2004. 78(12): p. 6297-303; Blanchard, P. et al., *Protection contre la maladie d'amaigrissement du porcelet (MAP) par vaccins a ADNet proteines recombinantes. Journees de la Recherche Porcine en France,* 2004. 36: p. 345-352; Blanchard, P., et al., *Protection of swine against porcine multisystemic wasting syndrome (PMWS) by porcine circovirus type 2 (PCV2) proteins. Vaccine,* 2003. 21: p. 4565-4575; Pogranichniy, R. et al. *Efficacy of inactivated PCV2 vaccines for preventing PMWS in CDCD pigs*. American Association of Swine Veterinarians. 2004. Des Moines, Iowa. However, an effective vaccine is not currently available.

The development of vaccines, diagnostic agents and therapies for PMWS and other diseases associated with PCV2 viral infections will require efficient and reliable means for producing the virus in substantial quantities. PCV2 virus stocks have conventionally been produced by culturing the virus in porcine kidney cell-line PK15. The virus titers yielded from PK15 cell cultures, expressed as 50% tissue culture infectious dosage ("$TCID_{50}$") per milliliter, usually ranged from $10^4$-$10^5$ and could never exceed $10^5$. Immunofluorescence stainings of infected PK15 cell cultures have revealed that only about 40% of the cell population is susceptible to the PCV2 infection.

A need exists for a continuous cell line that is highly permissive to PCV2 infection and that reliably produces virus in high titers over extended periods of time.

SUMMARY OF THE INVENTION

The present invention provides a continuous cell line that is highly permissive to PCV2 infection. In another embodiment, the invention provides a method for producing a substantially homogeneous cell line that is highly permissive to PCV2 infection, which comprises (1) cultivating a heterogeneous cell population that contains cells of varying susceptibility to PCV2 infection; (2) diluting the cell culture and placing aliquots of the diluted cells into separate vessels such that each vessel contains about one cell; (3) adding PCV2 to each vessel; (4) culturing the cells and identifying a vessel that contains cells that are susceptible to PCV2 infection; and (5) culturing and maintaining a cell line from such susceptible cells. In a particular embodiment, the invention provides a continuous cell line designated PK15-C1. In yet another embodiment, the invention provides a method for producing PCV2 by cultivating a virus in a cell line of the present invention under conditions suitable for cell growth and recovering virus produced by the cell line.

DETAILED DESCRIPTION OF THE INVENTION

In accordance with the invention, it has been discovered that the population of cells in the PK15 porcine kidney cell line is heterogeneous with respect to permissivity to the PCV2 infection. The cell line has been found to contain cells of both low- and high-permissivity to viral infection. The relatively low virus titers produced by PCV2-infected PK15 are attributable to the heterogeneity of the cell line.

Figure 1:
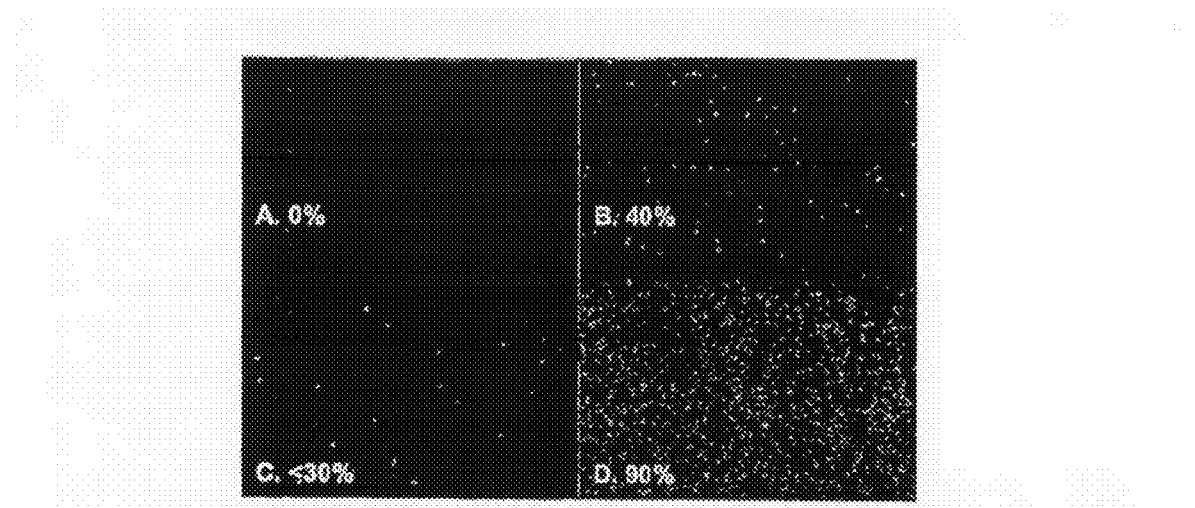
FIG. 1 shows immunofluorescence assay results demonstrating percentage infection on uncloned and cloned PK15 cell monolayers infected with PCV2 on 3 days post-infection. A, B, C and D represent mock-infected PK15 monolayer (negative control), infected PK15 monolayer, low-permissive and high-permissive (clone C1) subcloned monolayers respectively.
Figure 2:
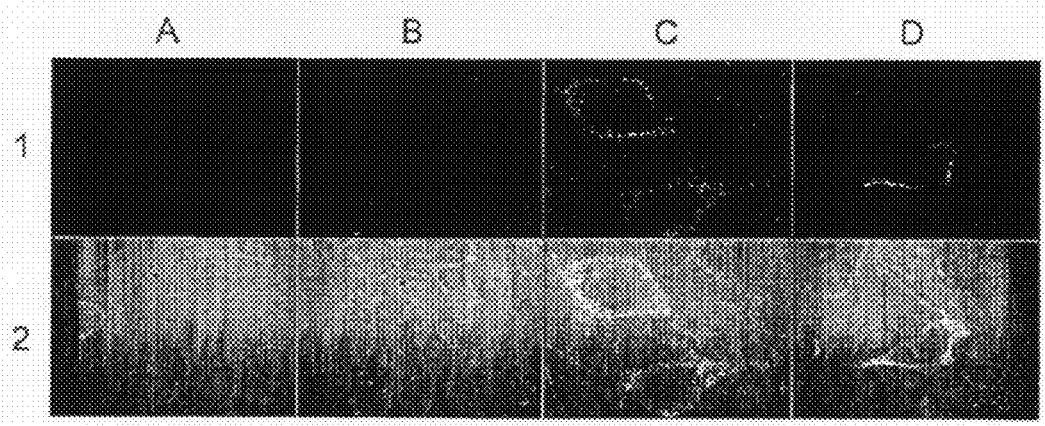
FIG. 2 shows PCV2 attachment onto surface membrane of PK15 cell line, low- and high-permissive cell clones after 1 hour adsorption at 37° C.
Figure 3:
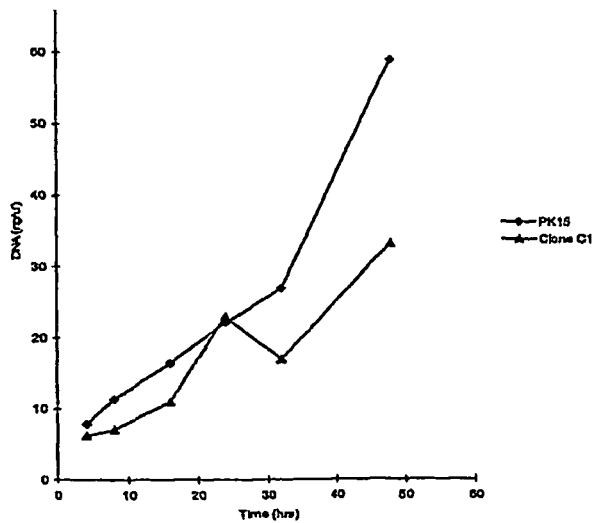
FIG. 3 shows growth curves of PK15 and clone C1 cell populations over 48 hours.
Figure 4:
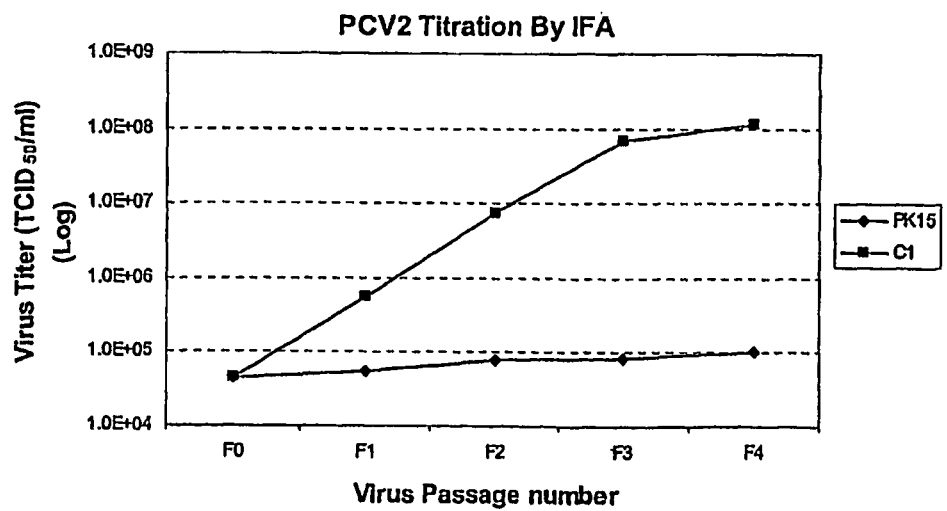
FIG. 4 shows PCV2 virus yields generated in parental PK15 and cloned C1 cell lines over 4 passages.

Homogeneous cell lines of this invention may be produced by cloning single cells and identifying resulting cultures that are highly susceptible to PCV2 infection. While the PK15 cell line is a preferred cell line for use in the methods of this invention, other cell lines that are susceptible to infection with PCV2 may also be used to produce homogeneous virus-producing cell lines.

A culture of a heterogeneous cell population is first diluted into aliquots containing single cells. The single-cell aliquots are placed into individual vessels, such as the wells of a microtiter plate, and are suspended in a nutrient medium that contains nutrients, growth factors and buffers necessary for replication of the cells. They are then incubated under thermal and atmospheric conditions conducive to cell growth. Following cell growth, e.g., to a continuous monolayer, an infectious amount of virus is added to each aliquot and the cells are cultured until a suitable phase of virus production is achieved.

Virus titers of each aliquot are determined, e.g., by immunofluorescence assay according to the following protocol: Infected cells are fixed with 4% paraformaldehyde for 15 minutes at 72 hours post-infection (pi), and incubated with PCV2 ORF-1 antibody followed by anti-guinea pig fluorescein isothyocianate (FITC), each for 1 hr at 37° C. with washing of cells one time with phosphate buffered saline between each step. The staining results are observed under an Olympus fluorescent microscope and cells are scored for their ability to produce high virus titers. High virus-producing cell lines are then advantageously re-cloned and highly permissive cells are selected.

A preferred cell line produced in accordance with the invention was derived from cell line PK15 (ATCC® CCL-33™ pig kidney cell line) and has been designated clone C1. It is referred to herein as PK15-C1. The results presented herein show that clonal C1 cell population is more susceptible to PCV2 infection than are PK15 cells. Therefore, PK15-C1 is a more effective cell line for the production of high PCV2 virus yield than the parental PK15 cell line.

PK15-C1 has been deposited with the American Type Culture Collection located at University Boulevard, Manassas, Va. 20110, USA on 20 Mar. 2007 and assigned accession number PTA-8244.

The invention is further illustrated by the following examples, which are not intended to limit the invention.

Example 1

Production of PK15-C1

The PK15 parent cell line was maintained in Eagle's minimum essential medium (MEM), supplemented with 5% fetal bovine serum (FBS), 2.2 g/L sodium bicarbonate, 2 mM L-glutamine, 1.0 mM sodium pyruvate and antibiotics. Cloning of PK15 cells was performed by the limiting-dilution method. The cells were trypsinized, diluted at a mean concentration of 1 cell/well in MEM/20% FBS/60% conditioned media and dispensed into 96-well tissue culture plates. The wells were immediately screened for single cells and marked, and the plates were incubated at 37° C. in an atmosphere of 5% $CO_2$. Following the identification of cell monolayers from the initial cloning, these subclones were subjected to another round of further cloning.

The PK15 parent and cloned cell populations were screened by immunofluorescence assay (IFA) for high- and low-permissive cells. The cells were seeded to 70% confluency in 96-well plates and infected with PCV2 with a titer of about $10^5$ $TCID_{50}$/ml at 6 hours post-seeding. Glucosamine (300 mM) was added to the infected cells within 24 hours of infection, and the cells were maintained in MEM/5% FBS at 37° C./5% $CO_2$. Positive and negative controls used in this experiment were PCV2 virus supernatant (s/n) of $10^5$ $TCID_{50}$/ml and MEM/5% FBS respectively. The cells were fixed with 4% paraformaldehyde, and IFA was performed at 72 hours post-infection (pi). IFA results demonstrated highest of 90% PCV2 infection in high-permissive clone C1 cells, compared to only 40% PCV2 infection in PK15 parent cells, and less than 20% infection in the remaining low-permissive cell clones (FIG. 1). In addition, a virus attachment assay was carried out to observe the affinity of PCV2 to the cell surface membrane of each cell clone. Each cell clone was seeded onto chamber slides and incubated overnight as above to obtain 70% confluency. PCV2 of $10^7$ $TCID_{50}$/ml was added to the cells for 1 hour adsorption at 37° C. and fixed with 4% paraformaldehyde. IFA was performed as above, however using PCV2 ORF-2 antibody for the primary antibody. After the final washing, the stained cells were mounted with fluorescent mounting media and observed under a Zeiss Meta inverted confocal microscope. Confocal microscopy results demonstrating PCV2 attachment onto cell surface membranes of cloned and uncloned PK15 cells after 1 hour adsorption at 37° C. are shown in FIG. 2. A, B, C and D represent mock-infected PK15 monolayer (negative control), infected low-permissive, high-permissive (clone C1) subcloned monolayers and infected PK15 monolayer respectively. 1) FITC fluorescent staining image. 2) Overlay of light phase and green fluorescence image. The spread and intensity of fluorescence, indicating PCV2 attachment to the cell surface membrane, was observed most intensely on high-permissive cell clone C1, followed by uncloned PK15 cells and low-permissive cell clones. These results suggested that clone C1 is most susceptible to PCV2 infection, and therefore selected for propagation of PCV2 virus.

Example 2

Characterization of PK15-C1

PK15 parent cells and clone C1 cells were characterized by their mean generation time in hours. Approximately $1\times10^5$ cells were seeded into 6-well plates, and cultured in MEM/10% FBS. The cells were trypsinized, counted, and underwent DNA extraction and quantitation at 0, 4, 8, 16, 24, 32 and 48 hours post-seeding. From the cell count and DNA quantitation data, the mean generation times of PK15 parent and clone C1 cell populations were determined to be 12.1 and 14.6 hours respectively. The results shown in FIG. 3 and Table 1 suggest that PK15 parent cells doubles faster than that of clone C1 cells.

Following, the titres for released virus in the culture supernatant were compared between virus yields from PK15 parent and clone C1 cells. The cells were seeded to 70% confluency in 150 $cm^2$ tissue culture flasks and infected with PCV2 ($10^4$ $TCID_{50}$/ml) at 6 hours post-seeding. The infected cultures were treated with D-glucosamine and maintained in culture media as previously mentioned. Finally, the virus-infected cultures were freeze-thawed three times at 4 days post infection (DPI), cells debris were pelleted at 3500 rpm at 4° C. for 5 minutes and supernatant containing PCV2 virus was retrieved. PCV2 virus was serially passaged in PK15 parent and clone C1 cell lines, harvested and stored at −80° C. until infectivity was determined by IFA using C1 clones. IFA results demonstrated that C1 cell clone produced a maximum virus titer of $10^8$ $TCID_{50}$/mL after 5 serial passages compared to a lower titer of $10^5$ $TCID_{50}$/mL generated from the parental PK15 cell line (FIG. 4).

TABLE 1

| Cell Line | Mean Generation Time (Hours) |
|---|---|
| PK15 | 12.1 |
| Clone C1 | 14.6 |

Figure 5:
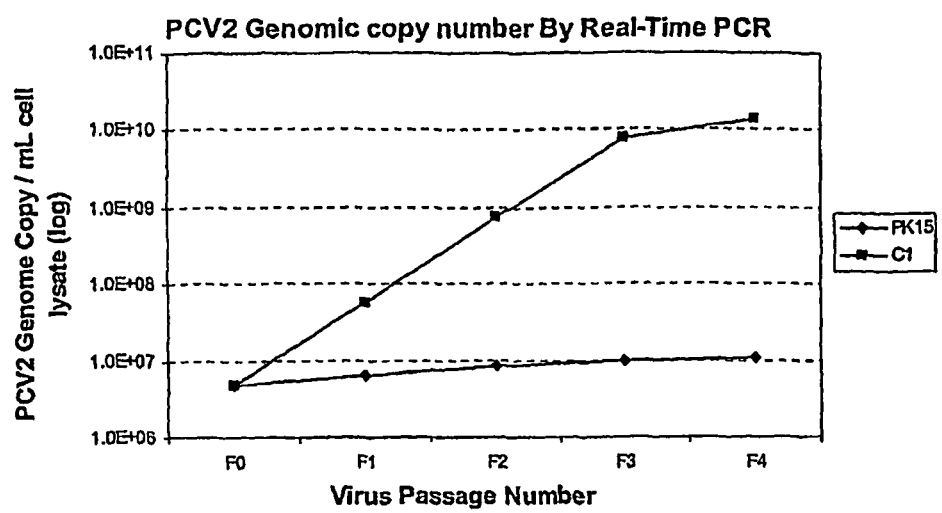
FIG. 5 shows PCV2 virus genome synthesis in parental PK15 and cloned C1 cell lines.

DNA replication rates of PCV2 in the parental PK15 and C1 cell clone were also assessed using a real-time PCR method. Two hundred microliters of each PCV2 infected PK15 and C1 cell lysate were harvested at 4 day post-infection (DPI) and DNA extractions were carried out using the QiaAmp DNA Mini kit (QIAGEN, Inc., Valencia, Calif. USA). The purified DNA was then eluted in 200 microliters of sterile distill water. Real-time PCR was carried out using the Roche LightCycler system (Roche Applied Science, Indianapolis, Ind. USA). One microliter of each DNA extract was used as PCR template and a pair of PCV2 specific primers was used for the amplification (Forward primer: 5' cacctggttgtggtaaaagc 3', Reverse primer: 5' ggtctgattgctggtaatcg 3'). A PBluescript plasmid (Stratagene, La Jolla, Calif. USA) containing PCV2 genome insert was used as standard reference. Real-time PCR quantification has shown that the genomic DNA copy number of PCV2 in 1 mL of PK15 and C1 cell lysates are $10^7$ and $10^{10}$ respectively (FIG. 5).

Although the invention has been described herein in detail for the purpose of illustration, it is to be understood that variations can be made therein by those skilled in the art without departing from the spirit and scope of the invention except as it may be limited by the claims.

We claim:

1. A method for the continuous production of porcine circovirus type 2 ("PCV2"), which comprises infecting a porcine kidney cell line PK15-C1 with said virus, growing said cell line under conditions suitable for cell growth; and recovering said virus produced by said cell line, wherein said porcine kidney cell line PK15-C1 is the cell line PK15-C1 deposited with the American Type Culture Collection on Mar. 20, 2007 as PTA-8244.

2. The cell line PK15-C1 deposited with the American Type Culture Collection on Mar. 20, 2007, as PTA-8244.

3. A porcine kidney cell line PK15-C1 for continually producing porcine circovirus type 2 ("PCV2"), wherein the cell line is produced by a method which comprises:
    (1) cultivating a heterogeneous PK15 cell population that contains cells of varying susceptibility to PCV2 infection;
    (2) diluting the cell culture and placing aliquots of the diluted cells into separate vessels such that each vessel contains about one cell;
    (3) adding PCV2 to each vessel;
    (4) culturing the cells and identifying a vessel that contains cells that are more permissive to PCV2 infection; and
    (5) culturing and maintaining a cell line from the more permissive cells identified in step 4,
    wherein said cell line from step 5 is the cell line PK15-C1 deposited with the American Type Culture Collection on Mar. 20, 2007, as PTA-8244.

* * * * *

UNITED STATES PATENT AND TRADEMARK OFFICE
CERTIFICATE OF CORRECTION

PATENT NO.        : 8,518,696 B2
APPLICATION NO.   : 12/599555
DATED             : August 27, 2013
INVENTOR(S)       : Lau et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 911 days.

Signed and Sealed this

Fifteenth Day of September, 2015

Michelle K. Lee
*Director of the United States Patent and Trademark Office*